United States Patent
Chou et al.

(10) Patent No.: US 9,612,241 B2
(45) Date of Patent: Apr. 4, 2017

(54) OPTICAL READOUT IMAGING SYSTEM AND BIOCHEMICAL DETECTION METHOD USING THE SAME

(71) Applicants: INDUSTRIAL TECHNOLOGY RESEARCH INSTITUTE, Chutung, Hsinchu (TW); CHANG GUNG MEMORIAL HOSPITAL, LINKOU, Gueishan Township, Taoyuan County (TW)

(72) Inventors: Pai-chien Chou, Guishan Township (TW); Bo-Wen Xiao, Luzhu (TW); Ming-Hua Yeh, Taipei (TW); Sin-Huei Wu, Caotun Township (TW)

(73) Assignees: INDUSTRIAL TECHNOLOGY RESEARCH INSTITUTE, Hsinchu (TW); CHANG GUNG MEMORIAL HOSPITAL, LINKOU, Gueishan Township, Taoyuan County (TW)

(*) Notice: Subject to any disclaimer, the term of this patent is extended or adjusted under 35 U.S.C. 154(b) by 193 days.

(21) Appl. No.: 14/576,470

(22) Filed: Dec. 19, 2014

(65) Prior Publication Data

US 2015/0276733 A1 Oct. 1, 2015

(30) Foreign Application Priority Data

Apr. 1, 2014 (TW) .............................. 103112096 A

(51) Int. Cl.
*G01N 33/561* (2006.01)

(52) U.S. Cl.
CPC ....... *G01N 33/561* (2013.01); *G01N 2550/00* (2013.01)

(58) Field of Classification Search
CPC ... G01N 2550/00; G01N 33/561; G01N 33/68

USPC ......... 436/86, 149, 150, 164, 165, 501, 535; 435/7.1; 422/68.1, 82.01, 82.05, 82.09; 204/450, 456, 461

See application file for complete search history.

(56) References Cited

U.S. PATENT DOCUMENTS

| | | | |
|---|---|---|---|
| 6,677,128 B1 | 1/2004 | Hanash et al. | |
| 7,166,441 B2 * | 1/2007 | Nadler | G01N 33/6851 204/464 |
| 7,170,605 B2 | 1/2007 | Cromwell et al. | |
| 7,525,523 B2 | 4/2009 | Yamazaki et al. | |
| 8,394,250 B2 * | 3/2013 | Margalit | G01N 27/44739 204/464 |

(Continued)

FOREIGN PATENT DOCUMENTS

| | | |
|---|---|---|
| CN | 101703923 A | 5/2010 |
| CN | 102918387 A | 2/2013 |
| CN | 102095867 B | 11/2013 |
| JP | 2006-317151 A | 11/2006 |
| JP | 3928073 B2 | 6/2007 |

(Continued)

OTHER PUBLICATIONS

TW Office Action dated Mar. 18, 2015. pp. 1-5.

(Continued)

*Primary Examiner* — Maureen Wallenhorst
(74) *Attorney, Agent, or Firm* — Birch, Stewart, Kolasch & Birch, LLP

(57) ABSTRACT

The present disclosure provides an optical readout imaging system may include first electrode, a thin film disposed on the first electrode, a biomolecule transfer layer disposed on the thin film, and a second electrode disposed on the biomolecule transfer layer. The present disclosure also provides a biochemical detection method using the optical readout imaging system.

16 Claims, 12 Drawing Sheets

(56) References Cited

U.S. PATENT DOCUMENTS

| | | |
|---|---|---|
| 2002/0008871 A1 | 1/2002 | Poustka et al. |
| 2009/0205979 A1 | 8/2009 | Bekki et al. |
| 2012/0103811 A1 | 5/2012 | Yung-Ping Chien et al. |
| 2012/0309024 A1* | 12/2012 | Margalit ............. G01N 33/561 435/7.9 |
| 2013/0115714 A1* | 5/2013 | Macnamara ..... G01N 27/44726 436/501 |

FOREIGN PATENT DOCUMENTS

| | | | |
|---|---|---|---|
| JP | 2010-107248 | * | 5/2010 |
| TW | 406190 B | | 9/2000 |

OTHER PUBLICATIONS

Andreotti et al., "Comparison of indirect ELISA based on recombinant protein NcSRS2 amd IFAT for detection of Neospora caninum antibodies in sheep", Rev. Bras. Parasitol. Vet., Jaboticabal, 2009, vol. 18, No. 2, pp. 19-22.

Cheng et al., "Paper-Based ELISA", Angew. Chem. Int. Ed., 2010, vol. 49, pp. 4771-4774.

Considine et al., "Enzyme Linked Immunosorbent Assay (ELISA) for the Determination of Protein-A", Bioscience Reports, 1986, vol. 6, No. 11, pp. 933-936.

Pospiech et al., "Comparison of the Results of the ELISA, Histochemical, and Immunohistochemical Detection of Soya Proteins in Meat Products", Czech J. Food Sci., 2011, vol. 29, No. 5, pp. 471-479.

Rencova et al., "ELISA for Detection of Soya Proteins in Meat Products", Acta Vet. Brno, 2009, vol. 78, pp. 667-671.

Wang et al., "Development of ELISA for the Determination of Transgenic Bt-Cottons Using Antibodies againts Cry1Ac Protein for Bacillus thuringiensis HD-73", Eng. Life Sci., 2007, vol. 7, No. 2, pp. 1-7.

* cited by examiner

S4

Instantly receiving the images of the proteins by an image sensor array — S4-1

FIG. 10

OPTICAL READOUT IMAGING SYSTEM AND BIOCHEMICAL DETECTION METHOD USING THE SAME

CROSS REFERENCE TO RELATED APPLICATIONS

This Application claims priority of Taiwan Patent Application No. 103112096, filed on Apr. 1, 2014, the entirety of which is incorporated by reference herein.

TECHNICAL FIELD

The technical field relates to an optical readout imaging system and a biochemical detection method using the same.

BACKGROUND

Western Blot is the technology widely applied in biochemistry, biomedical and biology research fields which evaluates the content of the specific protein in biological specimens through a gel battery and the theory of antibody detection and is capable of quantifying the trace targeted protein. The current Western Blot technology have caused problems such as image error and signal distortion, due to many manually controlled mechanisms and the inability to adjust voltage and current, making it impossible to locally apply voltage during the shifting process.

SUMMARY

One embodiment of the disclosure provides an optical readout imaging system comprising a first electrode, a thin film disposed on the first electrode, a biomolecule transfer layer disposed on the thin film, and a second electrode disposed on the biomolecule transfer layer.

One embodiment of the disclosure provides a biochemical detection method comprising providing the disclosed optical readout imaging system, adding a specimen to the biomolecule transfer layer, driving the second electrode to transfer the specimen from a first position to a second position in the biomolecule transfer layer, driving the second electrode and the first electrode to shift the specimen from the biomolecule transfer layer to the thin film, and coloring the specimen.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawing, wherein:

FIGS. 7-10 are detailed illustration of a procedure of the biochemical detection method in accordance with FIG. 6;

DETAILED DESCRIPTION

Figure 1:
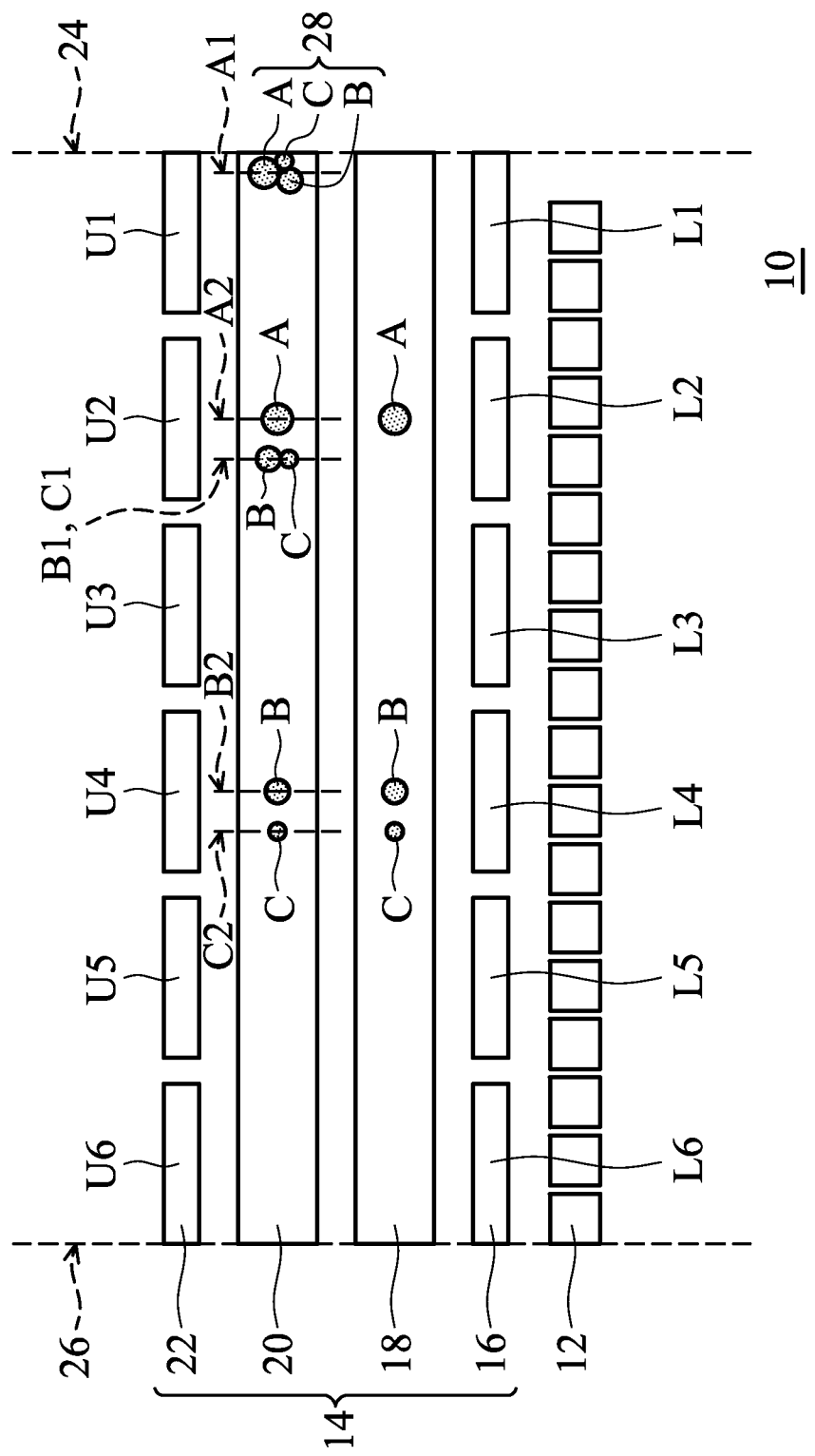
FIG. 1 is a diagram of an optical readout imaging system in accordance with the first embodiment of the disclosure.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Referring to FIG. 1, in accordance with the first embodiment of the disclosure, an optical readout imaging system is provided. An optical readout imaging system 10 comprises an image sensor array 12 and a detection unit 14. The detection unit 14 is disposed on the image sensor array 12. The detection unit 14 comprises a first electrode 16, a thin film 18, a biomolecule transfer layer 20 and a second electrode 22. The thin film 18 is disposed on the first electrode 16. The biomolecule transfer layer 20 is disposed on the thin film 18. The second electrode 22 is disposed on the biomolecule transfer layer 20.

The image sensor array 12 may comprise thin film transistors (TFTs), charge-coupled devices (CCDs) or complementary metal oxide semiconductor (CMOS). The first electrode 16 and the second electrode 22 may comprise indium tin oxide (ITO), aluminum-doped zinc oxide (AZO), indium zinc oxide (IZO), silver nanowire (SNW), carbon nanotube (CNT) or poly(3,4-ethylenedioxythiophene)/polystyrene sulfonate (PEDOT/PSS).

Figure 11:
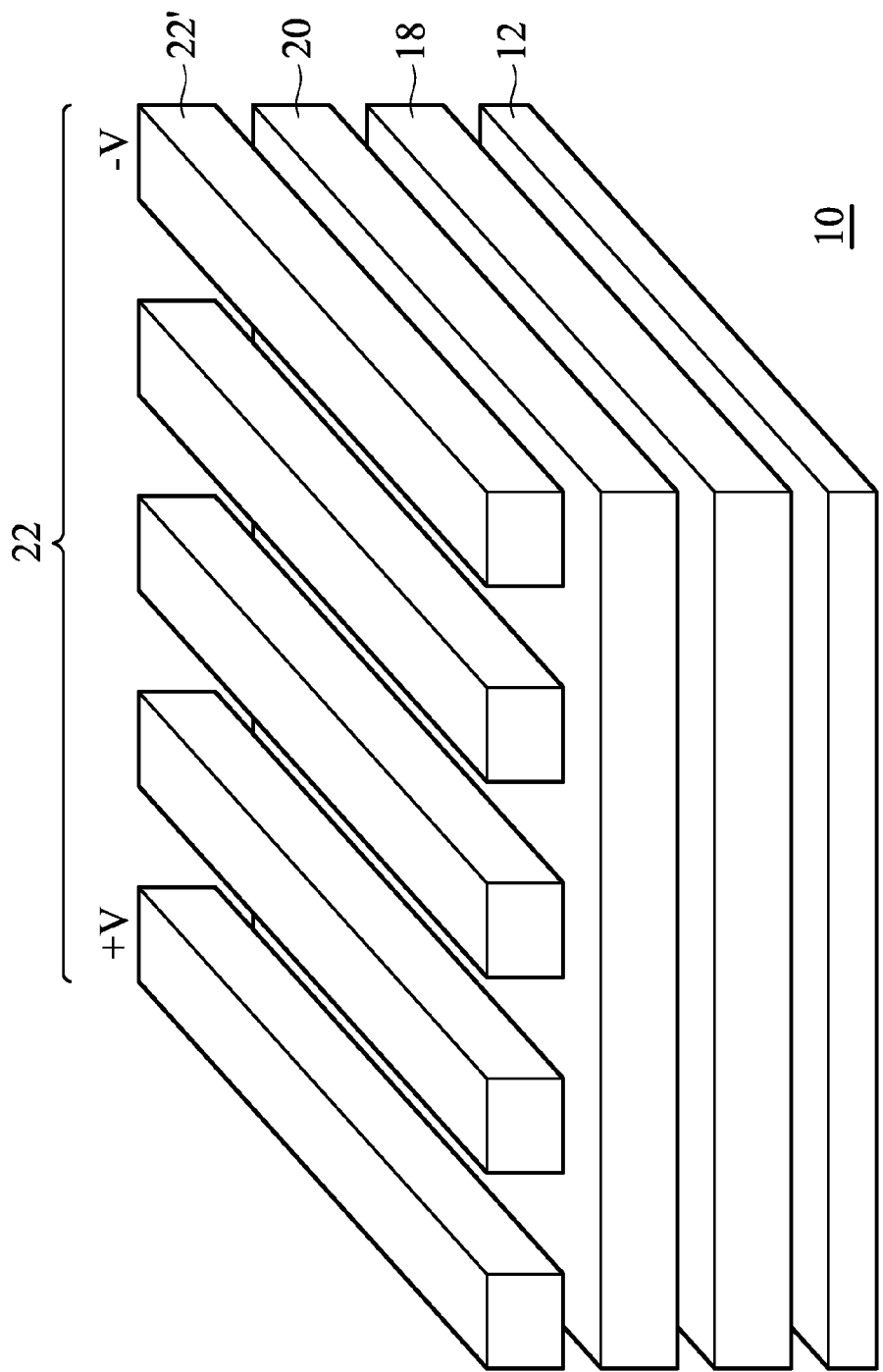
FIG. 11 is a sub-electrode array in strip form of an optical readout imaging system in accordance with one embodiment of the disclosure.
Figure 12:
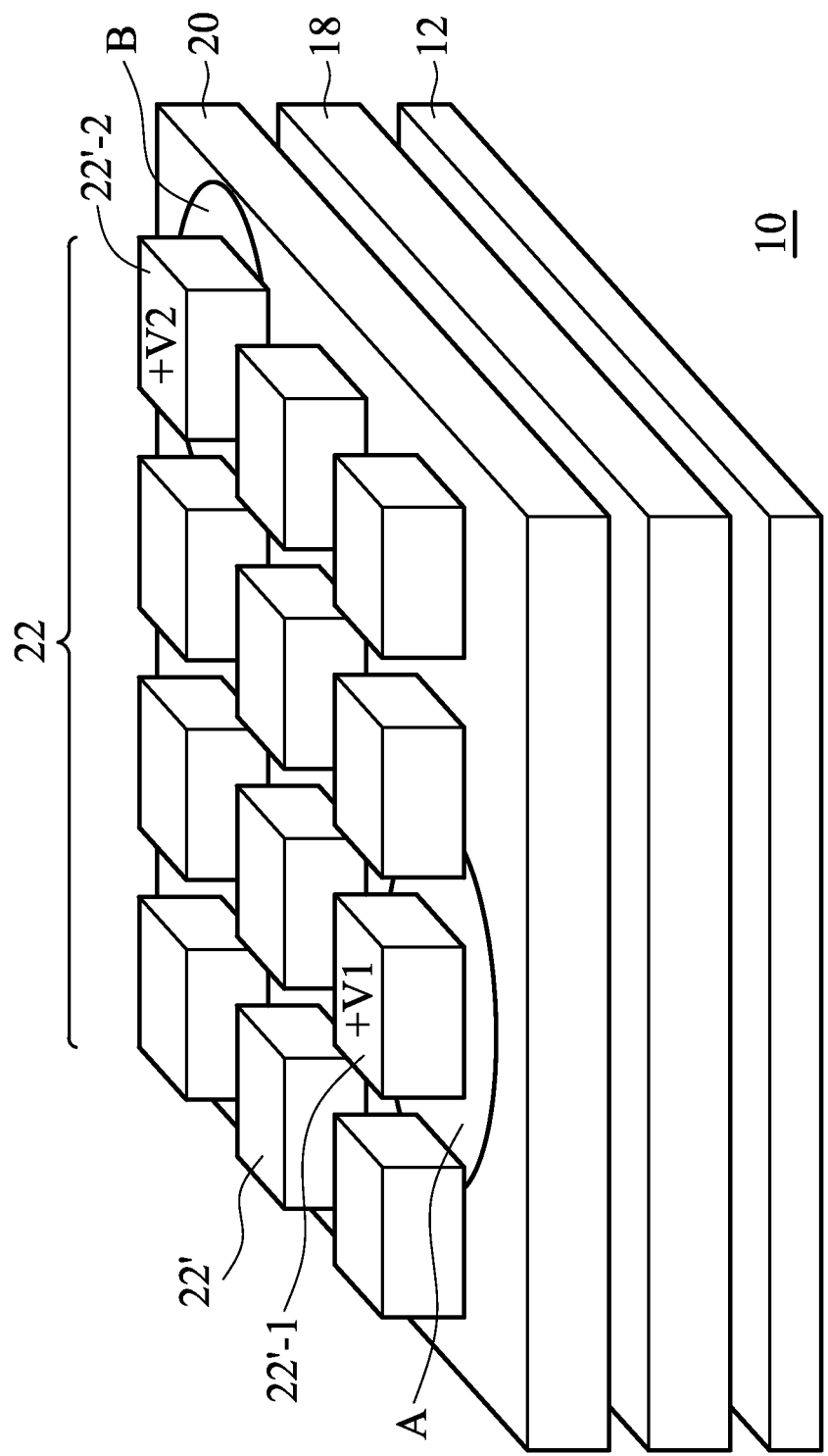
FIG. 12 is a sub-electrode array in spot form of an optical readout imaging system in accordance with one embodiment of the disclosure.

In some embodiments, the first electrode 16 and the second electrode 22 may respectively comprise an array of sub-electrodes 22' in strip form (referring to FIG. 11) or an array of sub-electrodes 22' in spot form (referring to FIG. 12).

The thin film 18 may comprise polyvinylidene difluoride (PVDF) or nitrocellulose (NC). The biomolecule transfer layer 20 may be an electrophoresis gel, for example, an SDS-PAGE.

In this embodiment, the first electrode 16 and the second electrode 22 respectively comprise a plurality of sub-electrodes (L1, L2, L3, L4, L5, L6, U1, U2, U3, U4, U5 and U6). The sub-electrodes are separated from each other and respectively arranged along from a starting point 24 of transferring to an end point 26 of transferring of the thin film 18 and the biomolecule transfer layer 20.

Figure 6:
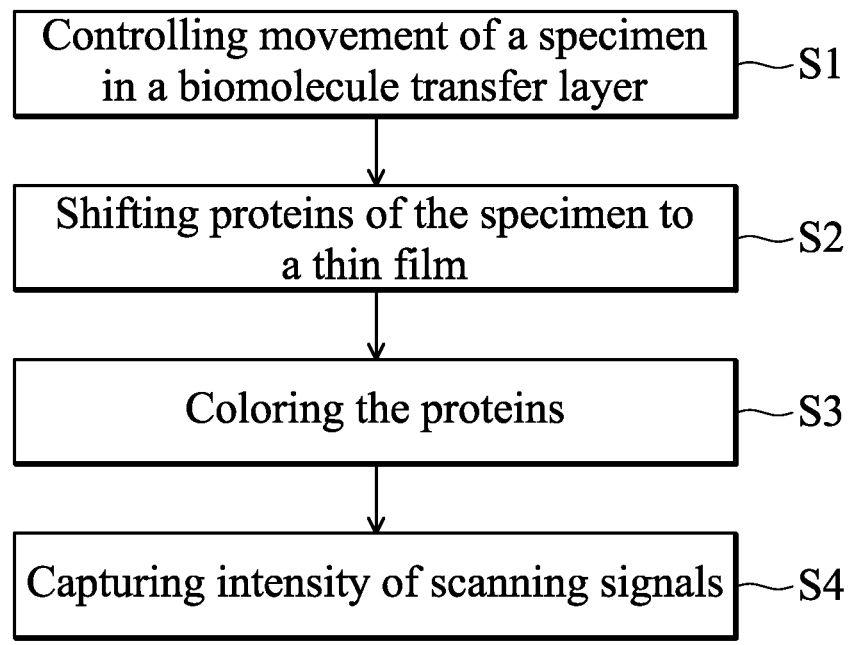
FIG. 6 is a flow chart of a biochemical detection method in accordance with one embodiment of the disclosure.

Referring to FIG. 6, FIG. 6 is a flow chart of a biochemical detection method of the disclosure, comprising four steps. Step S1 is controlling movement of a specimen in a biomolecule transfer layer. The specimen may comprise proteins. Step S2 is shifting proteins of the specimen to a thin film. Step S3 is coloring the proteins. Step S4 is capturing intensity of scanning signals.

Referring to FIGS. 1 and 6, in accordance with the first embodiment of the disclosure, a biochemical detection method is provided, described in detail below. The optical readout imaging system as shown in FIG. 1 is provided. A specimen 28 is added to the biomolecule transfer layer 20. The specimen 28 may comprise proteins or cells. In this embodiment, the specimen 28 comprises protein A, protein B and protein C. The second electrode 22 is driven to transfer protein A, protein B and protein C of the specimen 28 from a first position (A1, B1 and C1) to a second position (A2, B2 and C2) in the biomolecule transfer layer 20. The second electrode 22 and the first electrode 16 are simultaneously driven, for example, simultaneously applying a −V voltage on the sub-electrodes U1-U6 and applying a +V voltage on the sub-electrodes L1-L6 to shift the specimen 28 from the biomolecule transfer layer 20 to the thin film 18. The specimen 28 is colored. During the detection processes, the image sensor array 12 instantly captures optical signals of the specimen 28 in the biomolecule transfer layer 20 and the thin film 18 and outputs the optical signals to a device (not shown). The device receiving the optical signals may be a display device (such as a liquid-crystal display, a projector or a photo printer) or a memory device (such as random access memory or flash memory). The memory device may be further coupled to a readout device (such as disk).

The step of driving the second electrode 22 may comprise simultaneously driving the two sub-electrodes U1 and U2 of the second electrode 22 which respectively corresponds to the first position A1 and the second position A2 which the proteins, exemplary protein A, of the specimen 28 are located therein in the biomolecule transfer layer 20, for example, applying a −V voltage on the sub-electrode U1 and applying a +V voltage on the sub-electrode U2 to transfer the specimen 28, exemplary protein A, from the first position A1 to the second position A2 in the biomolecule transfer layer 20.

In one embodiment, referring to FIG. 12, the first electrode 16 (not shown) and the second electrode 22 respectively comprise an array of sub-electrodes 22' in spot form. The second electrode 22 is driven (for example, simultaneously driving any two sub-electrodes of the second electrode 22 (such as the sub-electrodes 22'-1 and 22'-2)), for example, applying a voltage (+V1) on the sub-electrode 22'-1 and applying another voltage (+V2) on the sub-electrode 22'-2 (two different voltages are—provided. When the proteins of the specimen, exemplary protein A and protein B, have different tropism towards the electrodes (for example, protein A having larger tropism than protein B towards the sub-electrode 22'-1 and protein B having larger tropism than protein A towards the sub-electrode 22'-2), and then, protein A moves to a position corresponding to the sub-electrode 22'-1 in the biomolecule transfer layer 20 and protein B moves to a position corresponding to the sub-electrode 22'-2 in the biomolecule transfer layer 20. In the specimen, numerous proteins having the same tropism as protein A towards the electrode aggregate in the position corresponding to the sub-electrode 22'-1 in biomolecule transfer layer 20. Similarly, numerous proteins having the same tropism as protein B towards the electrode aggregate in the position corresponding to the sub-electrode 22'-2 in biomolecule transfer layer 20, forming clusters of proteins. After forming the protein clusters, the tropism distribution of the proteins is observed by the image sensor array 12.

Referring to FIG. 1, the step of simultaneously driving the second electrode 22 and the first electrode 16 further comprises simultaneously driving the two sub-electrodes U2 and L2 of the second electrode 22 and the first electrode 16 which respectively corresponds to the second position A2 which the protein, exemplary protein A, of the specimen 28 is located therein in the biomolecule transfer layer 20, for example, applying a −V voltage on the sub-electrode U2 and applying a +V voltage on the sub-electrode L2, to shift the specimen 28, exemplary protein A, from the biomolecule transfer layer 20 to the thin film 18.

Figure 2:
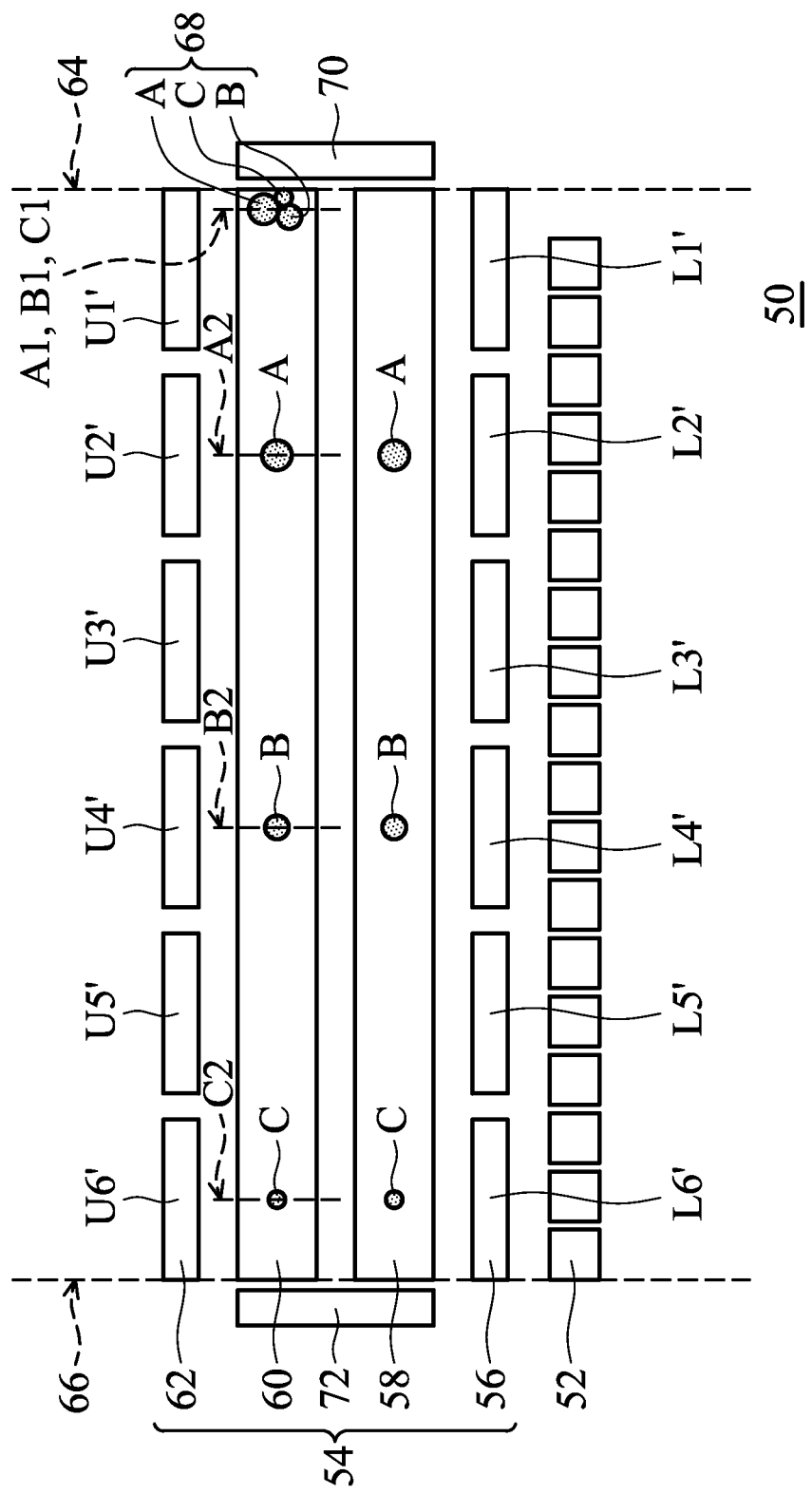
FIG. 2 is a diagram of an optical readout imaging system in accordance with the second embodiment of the disclosure.

Referring to FIG. 2, in accordance with the second embodiment of the disclosure, an optical readout imaging system is provided. An optical readout imaging system 50 comprises an image sensor array 52 and a detection unit 54. The detection unit 54 is disposed on the image sensor array 52. The detection unit 54 comprises a first electrode 56, a thin film 58, a biomolecule transfer layer 60 and a second electrode 62. The thin film 58 is disposed on the first electrode 56. The biomolecule transfer layer 60 is disposed on the thin film 58. The second electrode 62 is disposed on the biomolecule transfer layer 60.

The image sensor array 52 may comprise thin film transistors (TFTs), charge-coupled devices (CCDs) or a complementary metal oxide semiconductor (CMOS). The first electrode 56 and the second electrode 62 may comprise indium tin oxide (ITO), alumium-doped zinc oxide (AZO), indium zinc oxide (IZO), silver nanowire (SNW), carbon nanotube (CNT) or poly(3,4-ethylenedioxythiophene)/polystyrene sulfonate (PEDOT/PSS). The thin film 58 may comprise polyvinylidene difluoride (PVDF) or nitrocellulose (NC). The biomolecule transfer layer 60 may be an electrophoresis gel, for example, an SDS-PAGE.

In this embodiment, the first electrode 56 and the second electrode 62 respectively comprise a plurality of sub-electrodes (L1', L2', L3', L4', L5', L6', U1', U2', U3', U4', U5' and U6'). The sub-electrodes are separated from each other and respectively arranged along from a starting point 64 of transferring to an end point 66 of transferring of the thin film 58 and the biomolecule transfer layer 60. The optical readout imaging system 50 further comprises a third electrode 70 and a fourth electrode 72 respectively disposed outside the starting point 64 of transferring and the end point 66 of transferring of the thin film 58 and the biomolecule transfer layer 60. The third electrode 70 and the fourth electrode 72 are respectively a continuous electrode, as shown in FIG. 2.

Referring to FIGS. 2 and 6, in accordance with the second embodiment of the disclosure, a biochemical detection method is provided, described in detail below. The optical readout imaging system as shown in FIG. 2 is provided. A specimen 68 is added to the biomolecule transfer layer 60. The specimen 68 may comprise proteins or cells. In this embodiment, the specimen 68 comprises protein A, protein B and protein C. The third electrode 70 and the fourth electrode 72 are simultaneously driven, for example, applying a −V voltage on the third electrode 70 and applying a +V voltage on the fourth electrode 72, to transfer protein A, protein B and protein C of the specimen 68 from a first position (A1, B1 and C1) to a second position (A2, B2 and C2) in the biomolecule transfer layer 60. The second electrode 62 and the first electrode 56 are simultaneously driven, for example, simultaneously applying a −V voltage on the sub-electrodes U1'-U6' and applying a +V voltage on the sub-electrodes L1'-L6', to shift the specimen 68 from the biomolecule transfer layer 60 to the thin film 58. The specimen 68 is colored. During the detection processes, the image sensor array 52 instantly captures optical signals of the specimen 68 in the biomolecule transfer layer 60 and the thin film 58 and outputs the optical signals to a device (not shown). The device receiving the optical signals may be a display device (such as a liquid-crystal display, a projector or a photo printer) or a memory device (such as random access memory or flash memory). The memory device may be further coupled to a readout device (such as disk).

The step of simultaneously driving the second electrode 62 and the first electrode 56 further comprises simultaneously driving the two sub-electrodes U2' and L2' of the second electrode 62 and the first electrode 56 which respectively corresponds to the second position A2 which the protein, exemplary protein A, of the specimen 68 is located therein in the biomolecule transfer layer 60, for example, applying a −V voltage on the sub-electrode U2' and applying a +V voltage on the sub-electrode L2', to shift the specimen 68, exemplary protein A, from the biomolecule transfer layer 60 to the thin film 58.

Figure 3:
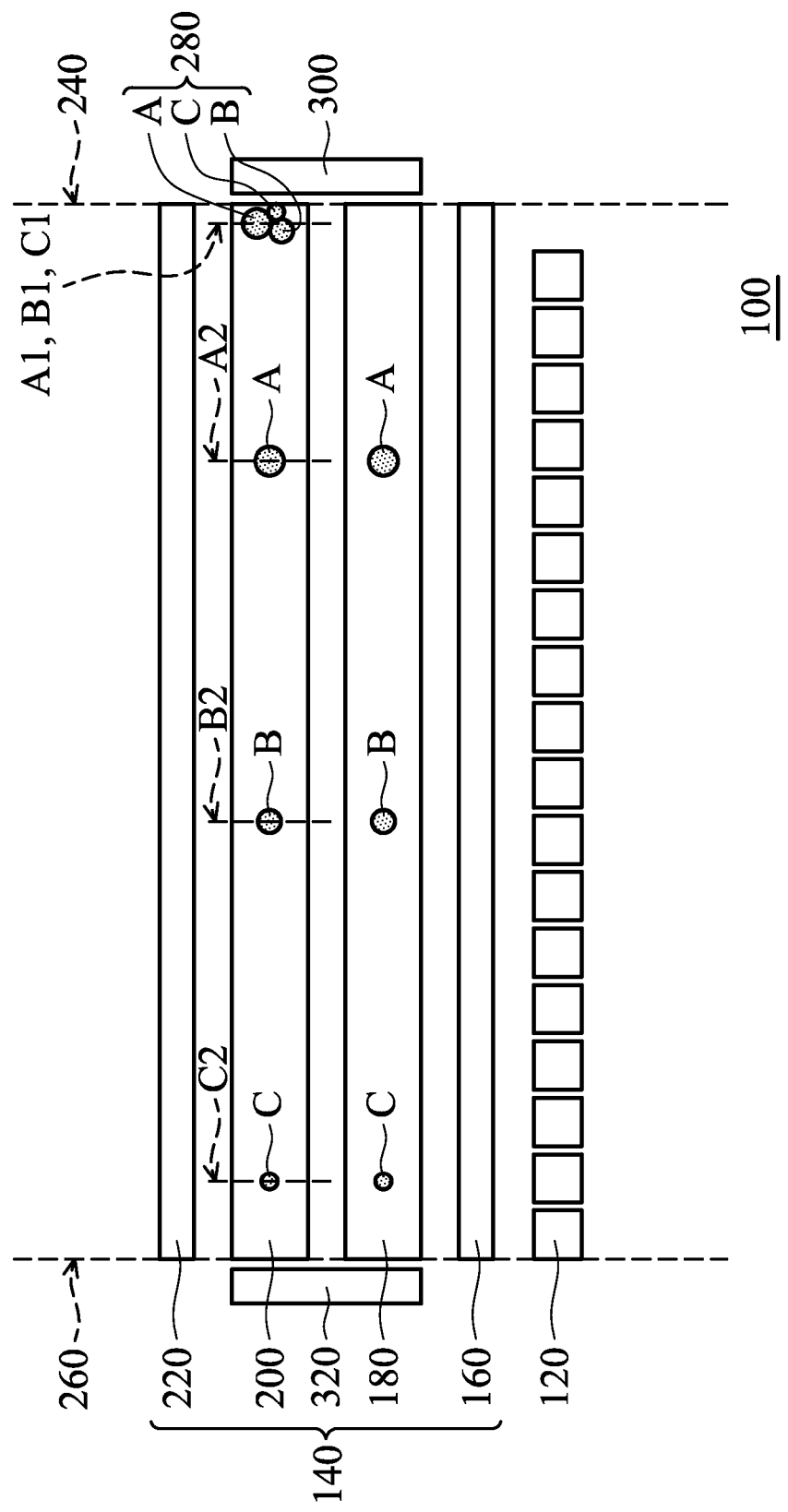
FIG. 3 is a diagram of an optical readout imaging system in accordance with the third embodiment of the disclosure.

Referring to FIG. 3, in accordance with the third embodiment of the disclosure, an optical readout imaging system is provided. An optical readout imaging system 100 comprises an image sensor array 120 and a detection unit 140. The detection unit 140 is disposed on the image sensor array 120. The detection unit 140 comprises a first electrode 160, a thin film 180, a biomolecule transfer layer 200 and a second electrode 220. The thin film 180 is disposed on the first electrode 160. The biomolecule transfer layer 200 is disposed on the thin film 180. The second electrode 220 is disposed on the biomolecule transfer layer 200.

The image sensor array 120 may comprise thin film transistors (TFTs), charge-coupled devices (CCDs) or complementary metal oxide semiconductor (CMOS). The first electrode 160 and the second electrode 220 may comprise indium tin oxide (ITO), alumium-doped zinc oxide (AZO), indium zinc oxide (IZO), silver nanowire (SNW), carbon nanotube (CNT) or poly(3,4-ethylenedioxythiophene)/polystyrene sulfonate (PEDOT/PSS). The thin film 180 may comprise polyvinylidene difluoride (PVDF) or nitrocellulose (NC). The biomolecule transfer layer 200 may be an electrophoresis gel, for example, an SDS-PAGE.

In this embodiment, the first electrode 160 and the second electrode 220 are respectively a continuous electrode and respectively extended from a starting point 240 of transferring to an end point 260 of transferring of the thin film 180 and the biomolecule transfer layer 200, as shown in FIG. 3. The optical readout imaging system 100 further comprises a third electrode 300 and a fourth electrode 320 respectively disposed outside the starting point 240 of transferring and the end point 260 of transferring of the thin film 180 and the biomolecule transfer layer 200. The third electrode 300 and the fourth electrode 320 are respectively a continuous electrode, as shown in FIG. 3.

Referring to FIGS. 3 and 6, in accordance with the third embodiment of the disclosure, a biochemical detection method is provided, described in detail below. The optical readout imaging system as shown in FIG. 3 is provided. A specimen 280 is added to the biomolecule transfer layer 200. The specimen 280 may comprise proteins or cells. In this embodiment, the specimen 280 comprises protein A, protein B and protein C. The third electrode 300 and the fourth electrode 320 are simultaneously driven, for example, applying a −V voltage on the third electrode 300 and applying a +V voltage on the fourth electrode 320, to transfer protein A, protein B and protein C of the specimen 280 from a first position (A1, B1 and C1) to a second position (A2, B2 and C2) in the biomolecule transfer layer 200. The second electrode 220 and the first electrode 160 are simultaneously driven, for example, applying a −V voltage on the second electrode 220 and applying a +V voltage on the first electrode 160, to shift the specimen 280 from the biomolecule transfer layer 200 to the thin film 180. The specimen 280 is colored. During the detection processes, the image sensor array 120 instantly captures optical signals of the specimen 280 in the biomolecule transfer layer 200 and the thin film 180 and outputs the optical signals to a device (not shown). The device receiving the optical signals may be a display device (such as a liquid-crystal display, a projector or a photo printer) or a memory device (such as random access memory or flash memory). The memory device may be further coupled to a readout device (such as disk).

Figure 4:
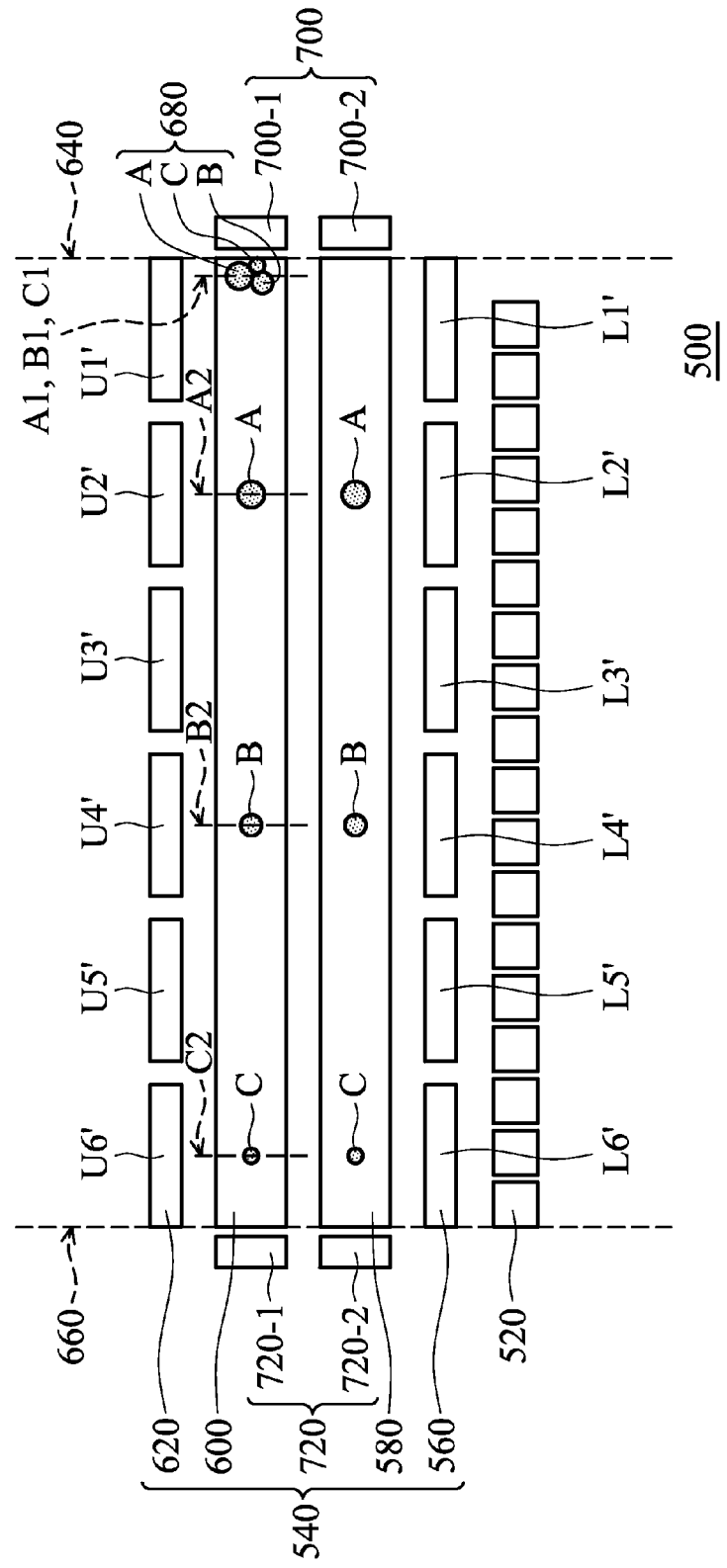
FIG. 4 is a diagram of an optical readout imaging system in accordance with the fourth embodiment of the disclosure.

Referring to FIG. 4, in accordance with the fourth embodiment of the disclosure, an optical readout imaging system is provided. An optical readout imaging system 500 comprises an image sensor array 520 and a detection unit 540. The detection unit 540 is disposed on the image sensor array 520. The detection unit 540 comprises a first electrode 560, a thin film 580, a biomolecule transfer layer 600 and a second electrode 620. The thin film 580 is disposed on the first electrode 560. The biomolecule transfer layer 600 is disposed on the thin film 580. The second electrode 620 is disposed on the biomolecule transfer layer 600.

The image sensor array 520 may comprise thin film transistors (TFTs), charge-coupled devices (CCDs) or complementary metal oxide semiconductor (CMOS). The first electrode 560 and the second electrode 620 may comprise indium tin oxide (ITO), alumium-doped zinc oxide (AZO), indium zinc oxide (IZO), silver nanowire (SNW), carbon nanotube (CNT) or poly(3,4-ethylenedioxythiophene)/polystyrene sulfonate (PEDOT/PSS). The thin film 580 may comprise polyvinylidene difluoride (PVDF) or nitrocellulose (NC). The biomolecule transfer layer 600 may be an electrophoresis gel, for example, an SDS-PAGE.

In this embodiment, the first electrode 560 and the second electrode 620 respectively comprise a plurality of sub-electrodes (L1', L2', L3', L4', L5', L6', U1', U2', U3', U4', U5' and U6'). The sub-electrodes are separated from each other and respectively arranged along from a starting point 640 of transferring to an end point 660 of transferring of the thin film 580 and the biomolecule transfer layer 600. The optical readout imaging system 500 further comprises a third electrode 700 and a fourth electrode 720 respectively disposed outside the starting point 640 of transferring and the end point 660 of transferring of the thin film 580 and the biomolecule transfer layer 600. The third electrode 700 and the fourth electrode 720 respectively comprise a plurality of sub-electrodes (700-1, 700-2, 720-1 and 720-2). The sub-electrodes are separated from each other and respectively corresponding to the thin film 580 and the biomolecule transfer layer 600, as shown in FIG. 4.

Referring to FIGS. 4 and 6, in accordance with the fourth embodiment of the disclosure, a biochemical detection method is provided, described in detail below. The optical readout imaging system as shown in FIG. 4 is provided. A specimen 680 is added to the biomolecule transfer layer 600. The specimen 680 may comprise proteins or cells. In this embodiment, the specimen 680 comprises protein A, protein B and protein C. The third electrode 700 and the fourth electrode 720 are simultaneously driven, for example, applying a −V voltage on the sub-electrode 700-1 (corresponding to the biomolecule transfer layer 600) and applying a +V voltage on the sub-electrode 720-1 (corresponding to the biomolecule transfer layer 600), to transfer protein A, protein B and protein C of the specimen 680 from a first position (A1, B1 and C1) to a second position (A2, B2 and C2) in the biomolecule transfer layer 600. The second electrode 620 and the first electrode 560 are simultaneously driven, for example, simultaneously applying a −V voltage on the sub-electrodes U1'-U6' and applying a +V voltage on the sub-electrodes L1'-L6', to shift the specimen 680 from the biomolecule transfer layer 600 to the thin film 580. The specimen 680 is colored. During the detection processes, the image sensor array 520 instantly captures optical signals of the specimen 680 in the biomolecule transfer layer 600 and the thin film 580 and outputs the optical signals to a device (not shown). The device receiving the optical signals may be a display device (such as a liquid-crystal display, a projector or a photo printer) or a memory device (such as random access memory or flash memory). The memory device may be further coupled to a readout device (such as disk).

The step of simultaneously driving the second electrode 620 and the first electrode 560 further comprises simultaneously driving the two sub-electrodes U2' and L2' of the second electrode 620 and the first electrode 560 which respectively corresponds to the second position A2 which the protein, exemplary protein A, of the specimen 680 is located therein in the biomolecule transfer layer 600, for example, applying a −V voltage on the sub-electrode U2' and applying a +V voltage on the sub-electrode L2', to shift the specimen 680, exemplary protein A, from the biomolecule transfer layer 600 to the thin film 580.

Figure 5:
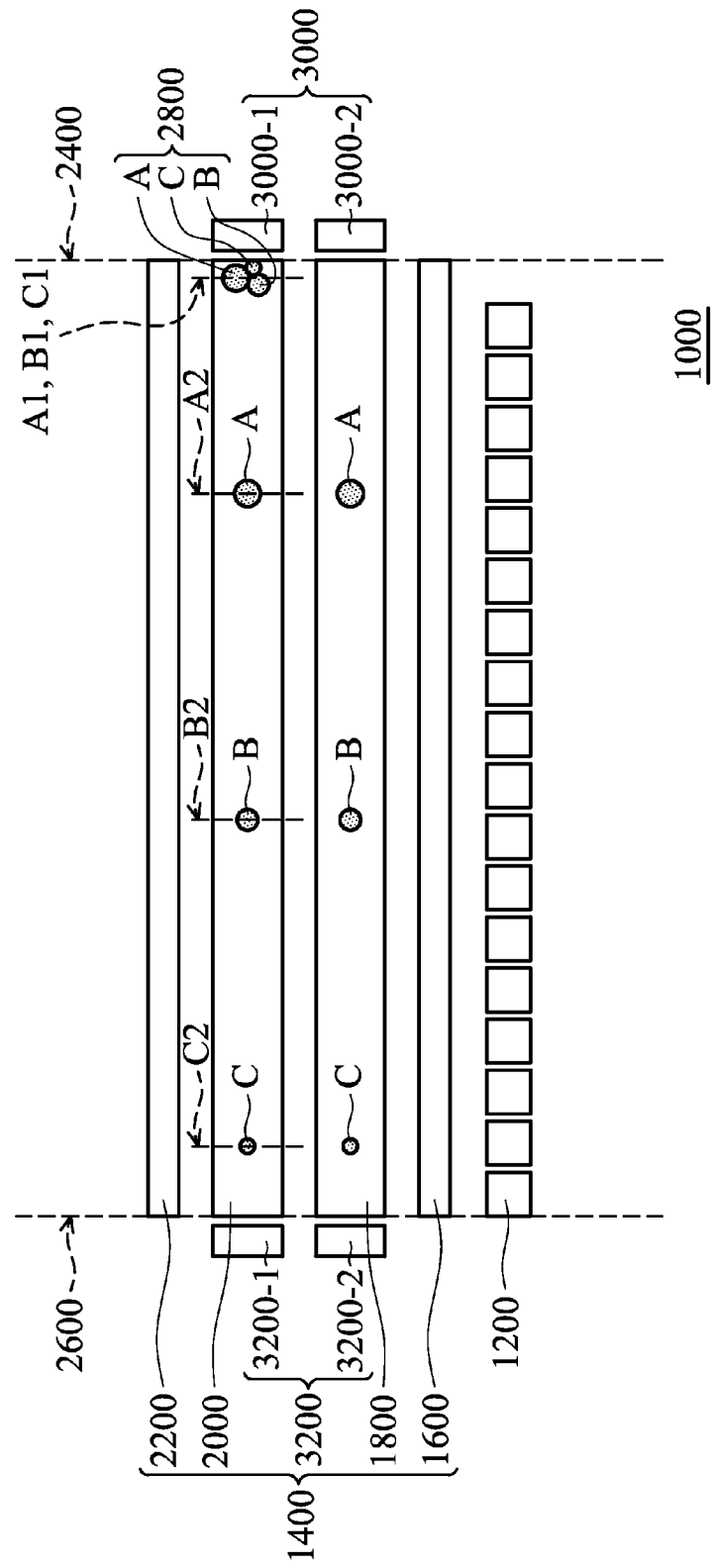
FIG. 5 is a diagram of an optical readout imaging system in accordance with the fifth embodiment of the disclosure.

Referring to FIG. 5, in accordance with the fifth embodiment of the disclosure, an optical readout imaging system is provided. An optical readout imaging system 1000 comprises an image sensor array 1200 and a detection unit 1400. The detection unit 1400 is disposed on the image sensor array 1200. The detection unit 1400 comprises a first electrode 1600, a thin film 1800, a biomolecule transfer layer 2000 and a second electrode 2200. The thin film 1800 is disposed on the first electrode 1600. The biomolecule transfer layer 2000 is disposed on the thin film 1800. The second electrode 2200 is disposed on the biomolecule transfer layer 2000.

The image sensor array 1200 may comprise thin film transistors (TFTs), charge-coupled devices (CCDs) or complementary metal oxide semiconductor (CMOS). The first electrode 160 and the second electrode 220 may comprise indium tin oxide (ITO), alumium-doped zinc oxide (AZO), indium zinc oxide (IZO), silver nanowire (SNW), carbon nanotube (CNT) or poly(3,4-ethylenedioxythiophene)/polystyrene sulfonate (PEDOT/PSS). The thin film 1800 may comprise polyvinylidene difluoride (PVDF) or nitrocellulose (NC). The biomolecule transfer layer 2000 may be an electrophoresis gel, for example, an SDS-PAGE.

In this embodiment, the first electrode 1600 and the second electrode 2200 are respectively a continuous electrode and respectively extended from a starting point 2400 of transferring to an end point 2600 of transferring of the thin film 1800 and the biomolecule transfer layer 2000, as shown in FIG. 5. The optical readout imaging system 1000 further comprises a third electrode 3000 and a fourth electrode 3200 respectively disposed outside the starting point 2400 of transferring and the end point 2600 of transferring of the thin film 1800 and the biomolecule transfer layer 2000. The third electrode 3000 and the fourth electrode 3200 respectively comprise a plurality of sub-electrodes (3000-1, 3000-2, 3200-1 and 3200-2). The sub-electrodes are separated from each other and respectively corresponding to the thin film 1800 and the biomolecule transfer layer 2000, as shown in FIG. 5.

Referring to FIGS. 5 and 6, in accordance with the fifth embodiment of the disclosure, a biochemical detection method is provided, described in detail below. The optical readout imaging system as shown in FIG. 5 is provided. A specimen 2800 is added to the biomolecule transfer layer 2000. The specimen 2800 may comprise proteins or cells. In this embodiment, the specimen 2800 comprises protein A, protein B and protein C. The third electrode 3000 and the fourth electrode 3200 are simultaneously driven, for example, applying a −V voltage on the sub-electrode 3000-1 (corresponding to the biomolecule transfer layer 2000) and applying a +V voltage on the sub-electrode 3200-1 (corresponding to the biomolecule transfer layer 2000), to transfer protein A, protein B and protein C of the specimen 2800 from a first position (A1, B1 and C1) to a second position (A2, B2 and C2) in the biomolecule transfer layer 2000. The second electrode 2200 and the first electrode 1600 are simultaneously driven, for example, applying a −V voltage on the second electrode 2200 and applying a +V voltage on the first electrode 1600, to shift the specimen 2800 from the biomolecule transfer layer 2000 to the thin film 1800. The specimen 2800 is colored. During the detection processes, the image sensor array 1200 instantly captures optical signals of the specimen 2800 in the biomolecule transfer layer 2000 and the thin film 1800 and outputs the optical signals to a device (not shown). The device receiving the optical signals may be a display device (such as a liquid-crystal display, a projector or a photo printer) or a memory device (such as random access memory or flash memory). The memory device may be further coupled to a readout device (such as disk).

Figure 7:
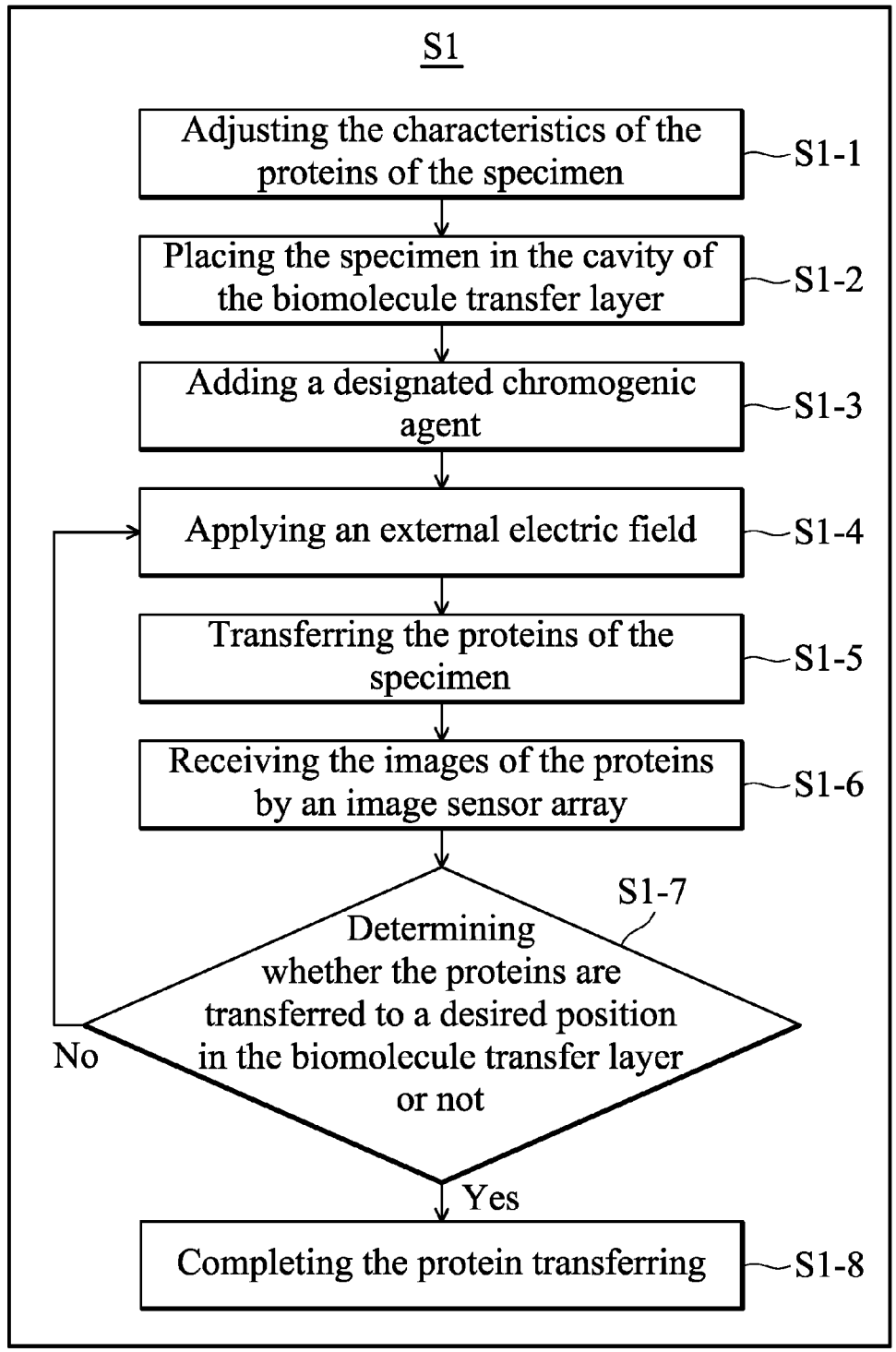
Figure 8:
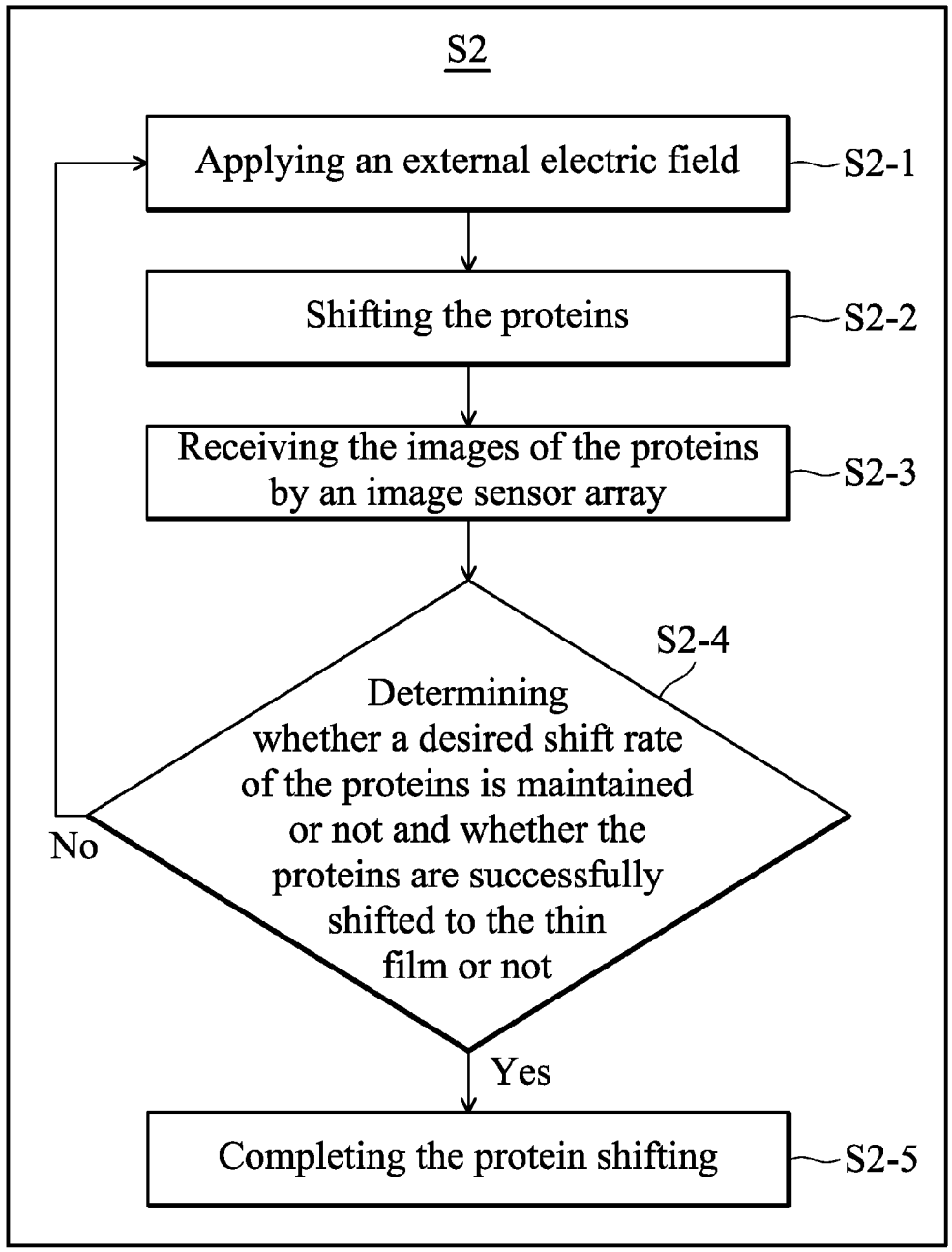
Figure 9:
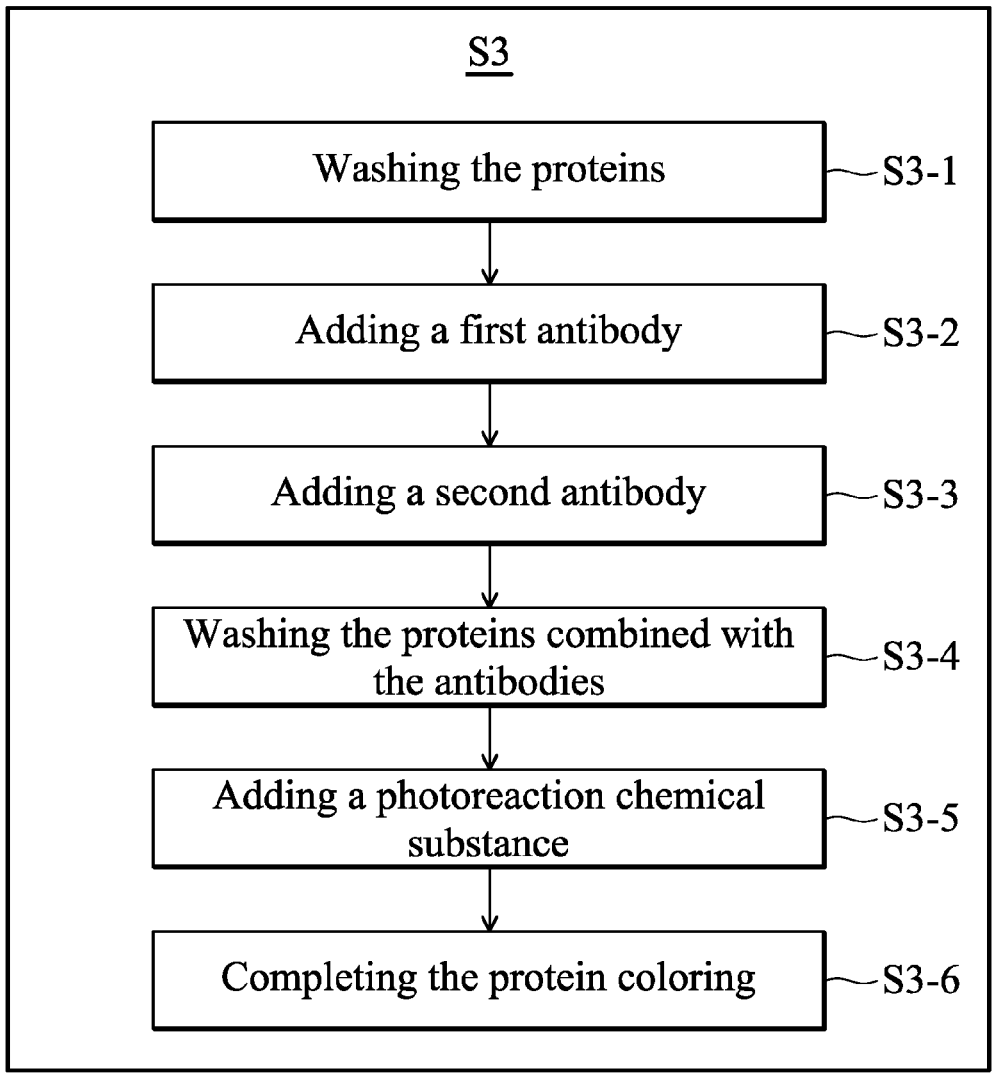

Referring to FIGS. 7-10, the four steps (S1-S4) of the procedure of the present biochemical detection method as shown in FIG. 6 are respectively described in detail below. Referring to FIG. 7, in step S1 of controlling movement of proteins of the specimen in the biomolecule transfer layer, The characteristics of the proteins of the specimen are adjusted (step S1-1). The specimen is placed in the cavity of the biomolecule transfer layer (step S1-2). A designated chromogenic agent is added (step S1-3). An external electric field is applied (step S1-4) to transfer the proteins of the specimen (step S1-5). The images of the proteins are received by an image sensor array (step S1-6), simultaneously. Whether the proteins are transferred to a position in the biomolecule transfer layer or not is determined (step S1-7). If the proteins are transferred to the position in the biomolecule transfer layer, the protein transferring is completed (step S1-8). If the proteins are not transferred to the position in the biomolecule transfer layer, the external electric field is adjusted until the proteins are transferred to the position in the biomolecule transfer layer.

In step S2 of shifting the proteins to the thin film, an external electric field is applied (step S2-1) to shift the proteins (step S2-2). The images of the proteins are received by the image sensor array (step S2-3), simultaneously. Whether a designated shift rate of the proteins is maintained or not and whether the proteins are successfully shifted to the thin film or not are determined (step S2-4). If the designated shift rate of the proteins is maintained and the proteins are successfully shifted to the thin film, the protein shifting is completed (step S2-5). If the designated shift rate of the proteins is not maintained and the proteins are not successfully shifted to the thin film, the external electric field is adjusted until the designated shift rate of the proteins is maintained and the proteins are successfully shifted to the thin film.

In step S3 of coloring the proteins, the proteins are washed (step S3-1). A first antibody is added (step S3-2). A second antibody is added (step S3-3). The proteins combined with the antibodies are washed (step S3-4). A photoreaction chemical substance is added (step S3-5). The protein coloring is completed (step S3-6).

In step S4 of capturing intensity of scanning signals, the image sensor array instantly receives the images of the proteins (step S4-1).

The present optical readout imaging system is capable of controlling the movement of proteins or cells on the biomolecule transfer layer or the thin film through applying various voltages to the transparent conductive electrodes. In the running step, a current parallel to the direction of TFT is applied to control movement of unknown protein specimen in the biomolecule transfer layer. In the shifting step, a current vertical to the direction of TFT is applied to shift the proteins from the biomolecule transfer layer to the thin film. The TFT image sensor array is, at any time, capable of monitoring the status of protein movement or separation from the running step to the coloring step and directly sensing images, and becomes an integrated instant-sensing device.

The role of the present TFT sensor array in the running step includes determining whether to stop applying voltage pursuant to the movement rate of the marker and decreasing voltage and current to avoid overheating when the movement of the marker is too fast. The role of the present TFT sensor array in the shifting step includes sensing whether the proteins are shifted from the biomolecule transfer layer to the thin film and intelligently adjusting voltage and current when the movement of the proteins is too slow.

The combination of the present optical readout imaging system and the TFT sensor array may have the following advantages. All reactions are directly operated on the TFT sensor array. The movement rate of the proteins on the biomolecule transfer layer is adjustable. The size of the biomolecule transfer layer is increasable for detecting more specimens.

Example

Detection of Proteins

Step 1: Controlling Movement of Proteins in the Biomolecule Transfer Layer

The optical readout imaging system 10 as shown in FIG. 1 and a specimen 28 were provided. The specimen 28 was a cluster of proteins (including protein A, protein B and protein C). The proteins of the specimen 28 were changed to unidirectional structures through chemical methods, and then denatured using SDS. All of the proteins were negatively charged. The specimen 28 was added to the biomolecule transfer layer 20. A designated chromogenic agent was added to color the proteins. A deeper color meant a higher concentration of the proteins. An appropriate external electric field was applied to simultaneously drive the two sub-electrodes U1 and U2 of the second electrode 22 which respectively corresponding to the first position A1 and the second position A2 which protein A of the specimen 28 was located therein in the biomolecule transfer layer 20, applying a −V voltage on the sub-electrode U1 and applying a +V voltage on the sub-electrode U2, and no applying voltage on the remaining sub-electrodes, to transfer protein A of the specimen 28 from the first position A1 to the second position A2 in the biomolecule transfer layer 20. The two sub-electrodes U2 and U4 of the second electrode 22 which respectively corresponding to the first position B1 and C1 and the second position B2 and C2 which proteins B and C of the specimen 28 were located therein in the biomolecule transfer layer 20 were simultaneously driven, applying a −V voltage on the sub-electrode U2 and applying a +V voltage on the sub-electrode U4, and no applying voltage on the remaining sub-electrodes, to transfer proteins B and C of the specimen 28 from the first position B1 and C1 to the second position B2 and C2 in the biomolecule transfer layer 20. The free-flow of denatured proteins was blocked due to their size being too large to pass through the suitably designed pore size of the biomolecule transfer layer 20. Under the appropriate external electric field, the same-size proteins with various quantities of charges generated differences in mobility such that the proteins were separated in the biomolecule transfer layer 20 through the characteristics of various sizes and charges of the proteins. The protein quantitation was focused on sensing intensity of optical signals. In accordance with the marker with known molecular weight, after flowing by applying current within a controlled time, the approximate position of the proteins having similar molecular weight with the marker in the biomolecule transfer layer 20 was recognized. Furthermore, the interested proteins stayed in particular positions in the gel through the control of current, facilitating subsequent analysis. In accordance with the task of monitoring images performed by the image sensor array 12, when the proteins were moved to the most suitable position for quantitative analysis (for example, the middle of the gel), the reaction was stopped.

Step 2: Shifting the Proteins to the Thin Film

An appropriate external electric field was applied to simultaneously drive the second electrode 22 and the first electrode 16, simultaneously applying a −V voltage on the sub-electrodes U1-U6 and applying a +V voltage on the sub-electrodes L1-L6 to shift the specimen 28 from the biomolecule transfer layer 20 to the thin film 18. In accordance with the characteristic of sensing optical signals provided by the image sensor array 12, whether the proteins were shifted from the biomolecule transfer layer 20 to the thin film 18 or not was perceived. The signal level was instantly recorded for feedback analysis to adjust voltage to avoid excessive voltage causing the proteins to move out the thin film 18. The protein size affected the shift efficiency. When the movement rate of the proteins was too slow, the voltage was increased, facilitating shifting of large-size proteins.

Step 3: Coloring the Proteins

The specimen 28 was colored. After automatic washing, a first antibody was added to identify the specific protein on the thin film 18. A second antibody bearing a luminescent substance capable of identifying the first antibody was appropriately bonded with the first antibody. After bonding for an appropriate time and washing, a designated chemical substance was added to react with the luminescent substance on the second antibody to produce color, more proteins, and more obvious coloring.

Step 4: Capturing Intensity of Scanning Signals

The image sensor array 12 instantly sensed and recorded intensity of optical signals during the coloring. An operator was able to go back at any time to seek the time point of the best signal-to-noise ratio due to the functionality of instant recording, avoiding errors in manual operation such as overexposure or underexposure.

During the detection processes, the image sensor array 12 instantly captured the optical signals of the specimen 28 in the biomolecule transfer layer 20 and the thin film 18 and outputted the optical signals to an external display device (not shown).

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An optical readout imaging system, comprising:
a first electrode;
a thin film disposed on the first electrode;
a biomolecule transfer layer disposed on the thin film;
a second electrode disposed on the biomolecule transfer layer;

an image sensor array disposed below the first electrode;
a third electrode disposed outside a starting point of transferring a specimen of the thin film and the biomolecule transfer layer; and
a fourth electrode disposed outside an end point of transferring the specimen of the thin film and the biomolecule transfer layer.

2. The optical readout imaging system as claimed in claim 1, wherein the first electrode and the second electrode respectively comprise a plurality of sub-electrodes, wherein the sub-electrodes are separated from each other and respectively arranged along from a starting point of transferring a specimen to an end point of transferring the specimen of the thin film and the biomolecule transfer layer.

3. The optical readout imaging system as claimed in claim 1, wherein the third electrode and the fourth electrode are respectively a continuous electrode.

4. The optical readout imaging system as claimed in claim 1, wherein the first electrode and the second electrode are respectively a continuous electrode and respectively extended from a starting point of transferring a specimen to an end point of transferring the specimen of the thin film and the biomolecule transfer layer.

5. The optical readout imaging system as claimed in claim 1, wherein the third electrode and the fourth electrode respectively comprise a plurality of sub-electrodes, wherein the sub-electrodes are separated from each other and one of each of the sub-electrodes is located at one end of the thin film and the biomolecule transfer layer.

6. A biochemical detection method, comprising:
providing an optical readout imaging system, wherein the optical readout imaging system comprises a first electrode, a thin film disposed on the first electrode, a biomolecule transfer layer disposed on the thin film, a second electrode disposed on the biomolecule transfer layer, an image sensor array disposed below the first electrode, a third electrode disposed outside a starting point of transferring a specimen of the thin film and the biomolecule transfer layer, and a fourth electrode disposed outside an end point of transferring the specimen of the thin film and the biomolecule transfer layer;
adding the specimen to the biomolecule transfer layer;
driving the third electrode and the fourth electrode to transfer the specimen from a first position to a second position in the biomolecule transfer layer;
driving the second electrode and the first electrode to shift the specimen from the biomolecule transfer layer to the thin film;
coloring the specimen when the specimen is located in the thin film; and
disposing an image sensor array below the first electrode to capture optical signals of the specimen and output the optical signals to a display device, a memory device or a computing device.

7. The biochemical detection method as claimed in claim 6, wherein the first electrode and the second electrode respectively comprise a plurality of sub-electrodes, wherein the sub-electrodes are separated from each other and respectively arranged along from a starting point of transferring a specimen to an end point of transferring the specimen of the thin film and the biomolecule transfer layer.

8. The biochemical detection method as claimed in claim 7, wherein in the step of driving the third electrode and the fourth electrode, two sub-electrodes of the second electrode which respectively correspond to the first position and the second position which the specimen is located therein in the biomolecule transfer layer are also driven.

9. The biochemical detection method as claimed in claim 7, wherein the step of driving the second electrode and the first electrode further comprises driving two sub-electrodes of the second electrode and the first electrode which respectively corresponds to the second position which the specimen is located therein in the biomolecule transfer layer.

10. The biochemical detection method as claimed in claim 6, wherein the image sensor array instantly captures the optical signals of the specimen in the biomolecule transfer layer and the thin film.

11. The biochemical detection method as claimed in claim 6, wherein when the first electrode and the second electrode respectively comprise a plurality of sub-electrodes, the sub-electrodes are separated from each other and the sub-electrodes are respectively arranged along from a starting point of transferring a specimen to an end point of transferring the specimen of the thin film and the biomolecule transfer layer, the step of driving the second electrode and the first electrode further comprises driving two sub-electrodes of the second electrode and the first electrode which respectively corresponds to the second position which the specimen is located therein in the biomolecule transfer layer.

12. The biochemical detection method as claimed in claim 6, wherein when the third electrode and the fourth electrode respectively comprise a plurality of sub-electrodes, the sub-electrodes are separated from each other and one of each of the sub-electrodes is located at one end of the thin film and the biomolecule transfer layer, the step of driving the third electrode and the fourth electrode comprises driving the sub-electrodes of the third electrode and the fourth electrode located at one end of the biomolecule transfer layer.

13. The biochemical detection method as claimed in claim 6, wherein the third and the fourth electrodes are controlled in accordance with a movement rate of the specimen to transfer the specimen to the second position in the biomolecule transfer layer.

14. The biochemical detection method as claimed in claim 13, wherein when the specimen is not transferred to the second position in the biomolecule transfer layer, the third and the fourth electrodes are controlled until the specimen is transferred to the second position.

15. The biochemical detection method as claimed in claim 6, wherein the second electrode and the first electrode are controlled in accordance with a shift rate of the specimen to maintain a designated shift rate of the specimen to successfully shift the specimen to the thin film.

16. The biochemical detection method as claimed in claim 15, wherein when the designated shift rate of the specimen is not maintained, the second electrode and the first electrode are controlled until the designated shift rate of the specimen is maintained and the specimen is successfully shifted to the thin film.

* * * * *